US007191663B2

(12) United States Patent
Go Boncan et al.

(10) Patent No.: US 7,191,663 B2
(45) Date of Patent: Mar. 20, 2007

(54) TESTING APPARATUS AND METHOD OF DERIVING YOUNG'S MODULUS FROM TENSILE STRESS/STRAIN RELATIONSHIPS

(75) Inventors: Virgilio Go Boncan, Spring, TX (US); Murray J. Rogers, Houston, TX (US); Thomas Heinold, Houston, TX (US); Robert L. Dillenbeck, Spring, TX (US)

(73) Assignee: BJ Services Company, Houston, TX (US)

( * ) Notice: Subject to any disclaimer, the term of this patent is extended or adjusted under 35 U.S.C. 154(b) by 89 days.

(21) Appl. No.: 10/734,873

(22) Filed: Dec. 12, 2003

(65) Prior Publication Data

US 2005/0126300 A1 Jun. 16, 2005

(51) Int. Cl.
*G01N 3/00* (2006.01)
(52) U.S. Cl. ....................................... 73/803
(58) Field of Classification Search ................ 73/784, 73/801, 767, 768, 587, 627, 766, 597
See application file for complete search history.

(56) References Cited

U.S. PATENT DOCUMENTS

| | | | | |
|---|---|---|---|---|
| 3,577,610 | A | * | 5/1971 | Margolin et al. ............ 425/99 |
| 3,742,757 | A | * | 7/1973 | Callahan .................. 73/88.5 R |
| 4,376,463 | A | | 3/1983 | Pattillo et al. |
| 4,389,896 | A | * | 6/1983 | Babcock ..................... 73/784 |
| 4,999,959 | A | * | 3/1991 | Virtanen ................... 52/223.14 |
| 5,741,971 | A | * | 4/1998 | Lacy ............................ 73/597 |
| 6,112,599 | A | * | 9/2000 | Maki, Jr. ...................... 73/801 |
| 6,591,690 | B1 | * | 7/2003 | Crockford ..................... 73/760 |

FOREIGN PATENT DOCUMENTS

| | | |
|---|---|---|
| EP | 0583977 A2 | 2/1994 |
| FR | 2799458 A1 | 4/2001 |

OTHER PUBLICATIONS

Altuna, Gustavo; Centurion, Sergio; Ipina, Juan E. Perez; "Variation of the Mechanical Properties for Cementing Slurries with Different Compositions"; SPE Latin American and Caribbean Petroleum Engineering Conference; Mar. 25-28, 2001; pp. 1-13; Society of Petroleum Engineers; Buenos Aires, Argentina.

(Continued)

*Primary Examiner*—Max Noori
*Assistant Examiner*—Octavia Davis
(74) *Attorney, Agent, or Firm*—Locke Liddell & Sapp LLP

(57) ABSTRACT

A method of testing and a tester apparatus to determine the axial stress and strain of cements under the temperature and pressures encountered by cement during use in wellbore environments. Using these stress and strain measurements, the Young's Modulus may be established for a material at the encountered temperature and pressure of the wellbore. By combining static tensile strength testing and elasticity measurements of cements, Young's Modulus values for different cement compositions under stresses that are similar to the conditions occurring in an actual wellbore are possible.

8 Claims, 8 Drawing Sheets

OTHER PUBLICATIONS

Ravi, K.; Bosma, M.; "Improve the Economics of Oil and Gas Wells by Reducing Cement Failure"; IADC/SPE Drilling Conference; Feb. 26-28, 2002; pp. 1-13; Society of Petroleum Engineers; Dallas, Texas, USA.

Stiles, David; Hollies, Doug; "Implementation of Advanced Cementing Techniques to Improve Long Term Zonal Isolation in Steam Assisted Gravity Drainage Wells"; 200 SPE International Thermal Operations and Heavy Oil Symposium and International Horizontal Well Technology Conference: Nov. 4-7, 2002; pp. 1-8; Society of Petroleum Engineers; Calgary. Canada.

Philippacopoulos, A.J.; Berndt, M. L.; "Mechanical Response and Characterization of Well Cements"; SPE Annual Techical Conference and Exhibition; Sep. 29-Oct. 2, 2002; pp. 1-8; Society of Petroleum Engineers; San Antonio, Texas, USA.

Thiercelin, M. J.; Dargaud, B.; Baret, J. F.; Rodriguez, W. J.; "Cement Design Based on Cement Mechanical Response"; 1997 Annual Technical Conference and Exhibition; Oct. 5-7, 1997; pp. 337-348; Society of Petroleum Engineers; San Antonio, Texas, USA.

Heinold, Thomas; Dillenbeck, Robert L.; Rogers, Murray J.; "The Effect of Key Cement Additives on the Mechanical Properties of Normal Density Oil and Gas Well Cement Systems"; SPE Asia Pacific Oil and Gas Conference and Exhibition; Oct. 8-10, 2002; pp. 1-12; Society of Petroleum Engineers; Melbourne, Australia.

Babasheikh, Amjad; Hun, Christian; Cunningham, Erick; Helou, Husam; "New Shock Resistant Cement Reduces the Required Time for Side-Tracking from Kick-Off Cement Plugs"; SPE/IADC Drilling Conference; Feb. 19-21, 2003; pp. 1-6; Society of Petroleum Engineers; Amsterdam, Netherlands.

Bosma, Martin; Ravi, Kris; Van Driel, Willem; Schreppers, Gerd Jan; "Design Approach to Sealant Selection for the Life of the Well"; 1999 SPE Annual Technical Conference and Exhibition; Oct. 3-6, 1999; pp. 1-14; Society of Petroleum Engineers; Houston, Texas, USA.

American Society for Testing and Materials; ATSM Standard C 496-96: Standard Test Method for Splitting Tensile Strength of Cylindrical Concrete Specimens; 1996; pp. 1-4; ATSM; West Conshohocken, Pennsylvania, USA.

American Society for Testing and Materials; ATSM Standard C 348-02: Standard Test Method for Flexural Strength of Hydraulic-Cement Mortars; 2002; pp. 1-6; ATSM; West Conshohocken, Pennsylvania, USA.

American Society for Testing and Materials; ATSM Standard C 293-02: Standard Test Method for Flexural Strength of Concrete (Using Simple Beam With Center-Point Loading); 2002; pp. 1-3; ATSM; West Conshohocken, Pennsylvania, USA.

* cited by examiner

TESTING APPARATUS AND METHOD OF DERIVING YOUNG'S MODULUS FROM TENSILE STRESS/STRAIN RELATIONSHIPS

FIELD OF THE INVENTION

The invention relates to testing methods and devices used for testing of the mechanical properties of cement including cement formed in wellbore environments.

BACKGROUND OF THE INVENTION

Cement is used in the casing and liners of a wellbore. The annular space between the casing/lining and the wellbore is filled with a predetermined quantity of a cement mixture, which after hardening retains the casing/liner in place in the wellbore. The cement mixture is pumped in at the top end of the casing or liner, down to the lower end thereof and out into and up the annular space on the outside of the casing/liner.

Cementing is employed during many phases of wellbore operations. For example, cement may be employed to cement or secure various casing strings and/or liners in a well. Cementing may also be used to repair casing and/or to achieve formation isolation. Additionally, cementing may be employed during well abandonment. Cement operations performed in wellbores under these high stress conditions present problems including difficulty in obtaining wellbore isolation and maintaining the mechanical integrity of the wellbore.

In essence, cement is placed in the annulus created between the outside surface of a pipe string and the inside formation surface or wall of a wellbore in order to form a sheath to seal off fluid and/or solid production from formations penetrated by the wellbore. Cementing allows a wellbore to be selectively completed to allow production from, or injection into, one or more productive formations penetrated by the wellbore. Cement may be used for purposes including sealing off perforations, repairing casing leaks, plugging back or sealing off the lower section of a wellbore, or sealing the interior of a wellbore during abandonment operations.

Once established, this isolation may be impacted by the particular stresses associated with the environment found in the wellbore during operations. The cement sheath may be exposed to stresses imposed by well operations such as perforating, hydraulic fracturing, or high temperature-pressure differentials.

Furthermore, well cement compositions may be brittle when cured. These cement compositions may fail due to tensional and compressional stresses that are exerted on the set cement. These wellbore cements may be subjected to axial, shear, and compressional stresses. Relatively high temperatures may induce stress conditions and/or relatively high fluid pressures encountered inside cemented wellbore pipe strings during operations such as perforating, stimulation, injection, testing, or production. Moreover, stress conditions may be induced or aggravated by fluctuations or cycling in temperature or fluid pressures during similar operations. In addition, variations in temperature and internal pressure of the wellbore pipe string may result in radial and longitudinal pipe expansion and/or contraction which tends to place stress on the annular cement sheath existing between the outside surface of a pipe string and the inside formation surface or wall of a wellbore. In other cases, cements placed in wellbores are subjected to mechanical stress induced by vibrations and impacts resulting from operations.

Therefore, a need exists to be able to test the mechanical properties of cement such as the cement that is used in wellbore environments. This testing method needs to be able to accommodate the conditions that are found in the wellbore environment. The following testing method fail to provide a method of testing under these conditions.

Several testing methods have been developed to test various aspects of cement or concrete. For example, ASTM International has established the Standard Test Method for Flexural Strength of Concrete (Using Simple Beam With Center-Point Loading), Designation No. C 293-02. This test method purports to cover the determination of the flexural strength of concrete specimens by the use of a simple beam with center-point loading. The mechanism in this test employs a load-applying block and two specimen support blocks. Force is applied perpendicular to the face of the specimen until the specimen fails. The modulus of rupture is calculated as:

$$R = 3\, PL/2bd^2 \tag{1}$$

where:
R=Modulus of rupture, psi, or MPa,
P=maximum applied load indicated by the testing machine, lbf, or N,
L=span length, in., or mm,
b=average width of the specimen at the fracture, in., or mm, and
d=average depth of the specimen a the fracture, in., or mm.

This testing method only provides a modulus of rupture based on a perpendicular force being applied in surface ambient conditions. This testing method therefore fails to simulate the stresses encountered in the higher temperature and pressure conditions of the wellbore environment.

Additional standards have been developed for testing cement. For example ASTM International Standard Test Method for Flexural Strength of Hydraulic-Cement Mortars, Designation No. C 348-02 provides a centerpoint loading such that forces are applied to the specimen in a vertical direction to determine the flexural strength from the total maximum load as follows:

$$S_f = 0.0028\, P \tag{2}$$

where
$S_f$=flexural strength, Mpa, and
P=total maximum load, N.

This testing method only provides a flexural strength based on a vertical force being applied in surface ambient conditions to cause a total maximum load. This testing method therefore also fails to simulate the stresses encountered in the higher temperature and pressure conditions of the wellbore environment.

The standards also include a testing method to measure splitting tensile strength. For example ASTM International Standard Test Method for Splitting Tensile Strength of Cylindrical Concrete Specimens, Designation No. C 496-96 provides for applying a diametrical compressive force along the length of a cylindrical concrete specimen until failure of the specimen. The loading induces tensile stresses on the plane containing the applied load and relatively high compressive stresses in the area around the applied load. Tensile failure occurs rather than compressive failure because the areas of load application are in a state of triaxial compression. The splitting tensile strength of the specimen is calculated by the formula:

$$T = 2P/(\Pi l d) \quad (3)$$

where:

T=Tensile splitting strength, psi (kPa),

P=maximum applied load indicated by the testing machine, lbf (kN),

Π=3.1416 l=length, in. (m), and d=diameter, in. (m).

Similarly to the previously discussed testing methods, this testing method only provides a tensile splitting strength based on a diametrical compressive force applied in surface ambient conditions. This testing method therefore fails to simulate the stresses encountered in the higher temperature and pressure conditions of the wellbore environment.

Additionally, each of these standards specifically instructs the creation of the specimens at a temperature and pressure that is similar to ambient surface conditions. None of these testing methods provides for the creation of samples under the temperature and pressure conditions found in a wellbore environment.

Therefore a need exists for the formation and testing of cement under a simulation of the conditions found in a wellbore environment. Testing methods under these conditions will provide data that is more precise in providing for a method to determine the mechanical characteristics of the specimen.

SUMMARY OF THE INVENTION

Most cements fail in the annulus of a well while under tension or a combination of tension and compression (flexural stress). The ratio of axial stress to axial strain (Young's Modulus) needs to be examined when the axial stress is tensional or a combination of tension and compression.

The present invention offers a method of testing and a tester designed to test the stress and strain of cements under the temperature and pressures encountered by cement during use in wellbore environments. Using these stress and strain measurements, the Young's Modulus may be established for a material at the encountered temperature and pressure of the wellbore. Using this information, it is possible to derive a baseline for materials to be used in the wellbore environment.

Before conducting an induced stress analysis for a given cement system, it is important to quantify the mechanical properties of that set cement. Chief among these properties is the Young's Modulus of elasticity, which is defined by the ratio of axial stress to axial strain. Typically, for a given change in well conditions, the lower the Young's Modulus is for a cement system, the lower the induced stress on that cement will be. Accordingly, the elastic nature exhibited by cement under stress, but prior to mechanical failure, is as important for long-term annular isolation, as the actual maximum stress at which mechanical failure ultimately occurs. The present invention overcomes the problems associated with a conventional static Young's Modulus test, which is a time-consuming operation and is almost always done with the axial stress applied in a compressive mode- even though by most definitions, the Young's Modulus is a mechanical property pertaining to a materials response under tension.

The following provides a means to combine static flexural/tensile strength testing and elasticity measurements of cements. Since most cements fail in the annulus of a well while under tension, or a combination of tension and compression, the ratio of axial stress to axial strain is an important factor when the axial stress was in tension, or a combination of tension and compression instead of just testing in compression. Using a testing device based on these methods, the present invention can generate Young's Modulus values for different cement compositions under stresses that are similar to the conditions occurring in an actual wellbore. The present invention allows the user to calculate the induced stresses that would occur if the different systems were used in a well, and thus develop better fit for purpose designs.

The present invention includes the development of a testing apparatus that enables the user to first cure from a liquid state, and then determine the mechanical properties such as tensile strength of various cement slurry systems through non-ultrasonic, destructive methods, while maintaining confining pressure and temperature on the cement specimens for the duration of the curing and testing process. It is within the scope of the invention that the present apparatus allows for a more accurate testing of mechanical properties of oil and gas well cements to ensure the long term integrity of the cement sheath in a well bore for the entire operation life of a given well.

Since current ASTM testing is carried out under atmospheric conditions, this invention provides for an alternative means to accurately measure tensile strength of various cement systems under more realistic field conditions. The invention discloses an apparatus that allows for the elimination of data influenced by factors such as cooldown and depressurization of cured cement samples.

Devices employing the testing techniques of the present invention may be fully automated in such a way that real-time stress versus strain plots can be generated prior to the determination of ultimate mechanical failure values. This would allow for an increase in both the quantity and the quality of data presented to the clients. Moreover, the present invention provides for data consistency and reliability because a more uniform testing method for all cement systems can be employed and all test conditions and data recording may be microprocessor controlled. The multi-functionality of this apparatus allows the user to measure cement shear bond strength while maintaining confining pressure and temperature.

BRIEF DESCRIPTION OF THE DRAWINGS

The accompanying drawings, which are incorporated in and form a part of the specification, illustrate the embodiments of the present invention, and, together with the description, serve to explain the principles of the invention. In the drawings.

It is to be noted that the drawings illustrate only typical embodiments of the invention and are therefore not to be considered limiting of its scope, for the invention encompasses other equally effective embodiments.

DETAILED DESCRIPTION OF PREFERRED EMBODIMENT

Figure 1:
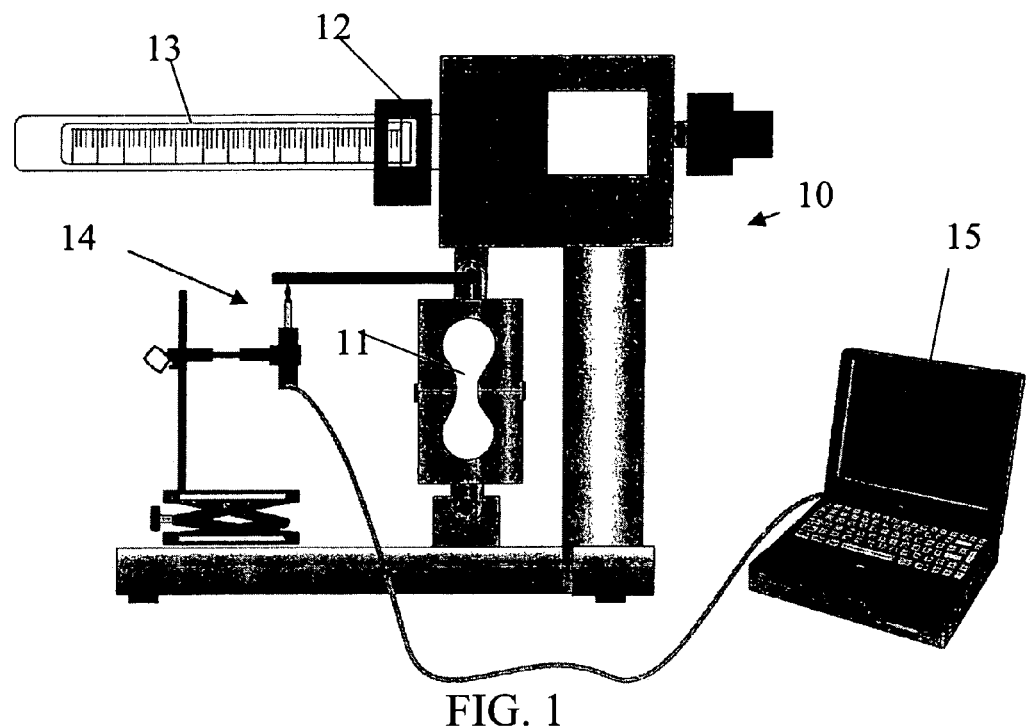
FIG. 1 is a representative diagram of an embodiment of a modified ASTM testing device that can test tensile strength, or with a different fixture, can test flexural strength.

Young's Modulus is a measurement of elasticity, which is defined by the ratio of axial stress to axial strain. The elastic nature exhibited by cement under stress, but prior to mechanical failure, is as important for long-term annular isolation, as the actual maximum stress at which mechanical failure ultimately occurs. FIG. 1 shows an embodiment of a flexural/tensile tester 10, which provides a means to combine static flexural/tensile strength testing and elasticity measurements of cements. As configured in the Figure, the tester 10 is configured for testing tensile strength, but can be modified to test flexural strength.

As previously discussed, most cements fail in the annulus of a well while under tension, or a combination of tension and compression. The ratio of axial stress to axial strain is therefore an important factor when the axial stress is in tension, or a combination of tension and compression.

The tester 10 may utilize a beam loading system for automatic testing of cement specimens 11 in flexure and for tensile tests. This tester 10 has a traveling weight 12, which is driven by electric motor across the beam 13 of the tester 10 to produce a constant rate of loading on the specimen 11. The beam 13 has dual scales. As depicted in FIG. 1, the tester 10 is a flexural/tensile tester made by Gilson Company. Those skilled in the art will recognize that any tester capable of flexural and tensile testing is with the scope of the invention. In this embodiment of the tester 10, the traveling weight 12 automatically stops upon specimen 11 failure and load is read directly from the applicable scale on the beam 13.

A sensor 14 is positioned in contact with the tester 10 such that the displacement may be measured and recorded. In the diagram shown herein, a computer 15 records the displacement measurements. This allows for calculations based not only of the force exerted at the time of failure of the specimen 11, but the displacement at the time of failure. The tester 10 provides a constant rate of loading, so the computer 15 may also plot the displacement versus time and/or calculate the loading versus displacement for a variety of calculations. A tester 10 can be used to generate Young's Modulus values for different cement compositions under stresses that are similar to the conditions occurring in an actual wellbore in a pressurized configuration.

The present invention includes the development of a testing apparatus that enables the user to first cure specimens 11 from a liquid state, and then determine the mechanical properties such as tensile strength and stress/strain relationships of various cement slurry systems through non-ultrasonic, destructive methods, while maintaining confining pressure and temperature on the cement specimens for the duration of the curing and testing process. It is within the scope of the invention that the present apparatus allows for a more accurate testing of mechanical properties of oil and gas well cements to ensure the long term integrity of the cement sheath in a well bore for the entire operation life of a given well.

Figure 2:
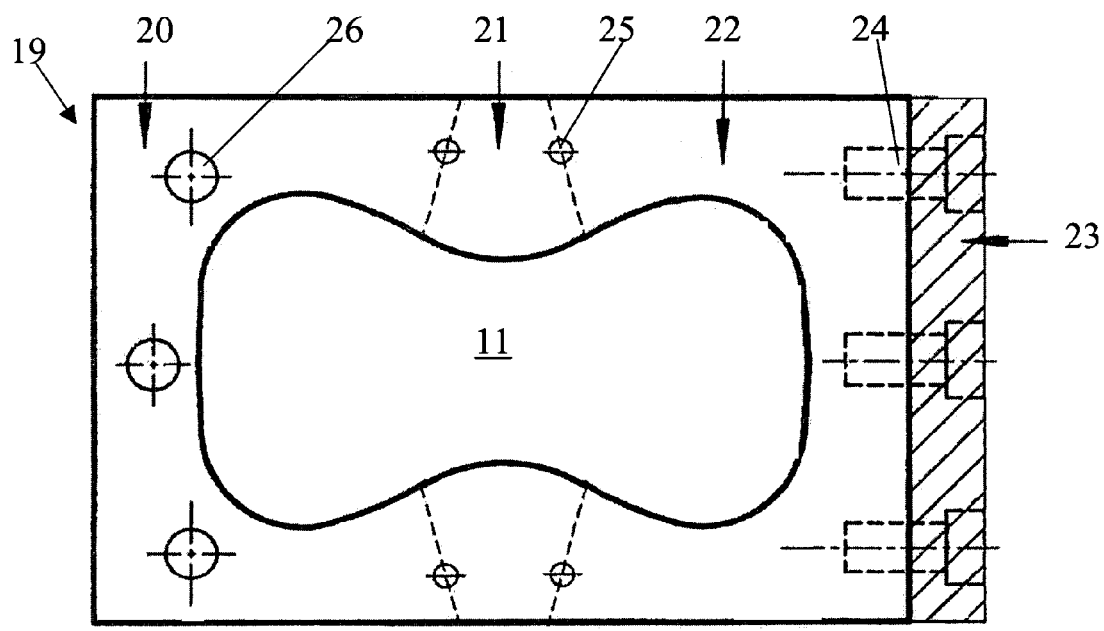
FIG. 2 is a diagram showing a component of the present invention.

As shown in FIG. 2, the cement specimen 11 is poured into a mold 19 having three sections: a mold stationary section 20, a mold floating section 21, and a mold follower section 22. The mold 19 can be inserted into a pressure chamber capable of simulating the temperature and pressure found in the wellbore environment. Pressures up to 3,000 psi and temperatures up to 500° F. can be encountered in this environment. Those skilled in the art will recognize that the current invention is capable of being used at any pressure greater than atmospheric pressure and with a temperature range of about 32° F. to about 500° F. By curing and then testing the specimen 11 under the temperature and pressure conditions found in a wellbore, it is possible to obtain more accurate data related to the strength of the specimen 11. As shown, specimen 11 is poured or formed in a shape similar to the one depicted in FIG. 2.

The follower portion 22 of the mold 19 is bolted or otherwise attached to the follower 23 at bolt locations 24. Moreover, alignment pins 25 align the mold stationary section 20, a mold floating section 21, and a mold follower section 22. Additionally, the mold stationary section 20 is bolted to the mold base 30, shown in FIG. 3 by base bolts 26. In operation, follower 23 pulls the mold follower section 22 away from the mold stationary section 20 and the mold floating section 21. The mold floating section 21 is designed to not exert any force of the specimen during testing. The mold stationary section 20, bolted to the mold base 30, remains stationary during testing.

Figure 3:
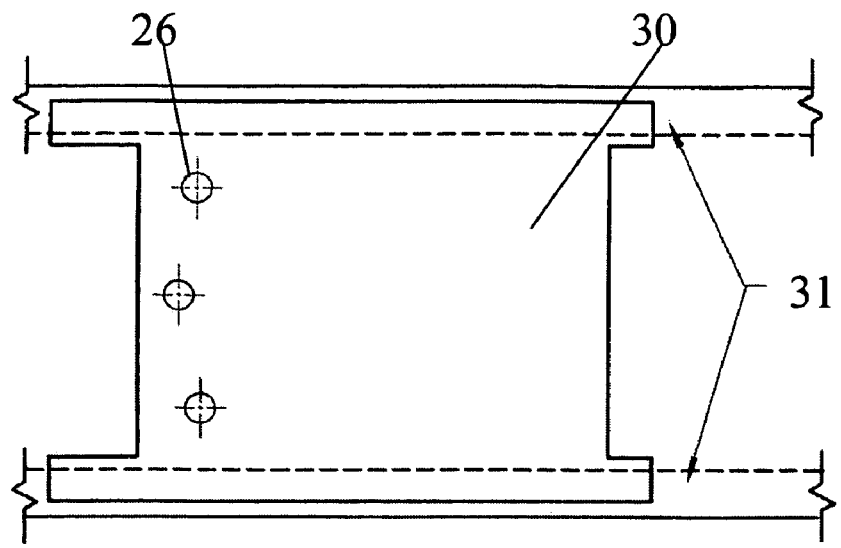
FIG. 3 is a diagram showing a component of the present invention.

Referring to FIG. 3, the mold base 30 is shown in greater detail. The base bolts 26, which connect the mold base 30 to the stationary section 20 of the mold 19, are shown. Moreover, the mold base 30 is anchored to railings 31. As shown in greater detail below, these railings 31 are anchored to the testing vessel and do not allow any movement.

Figure 4:
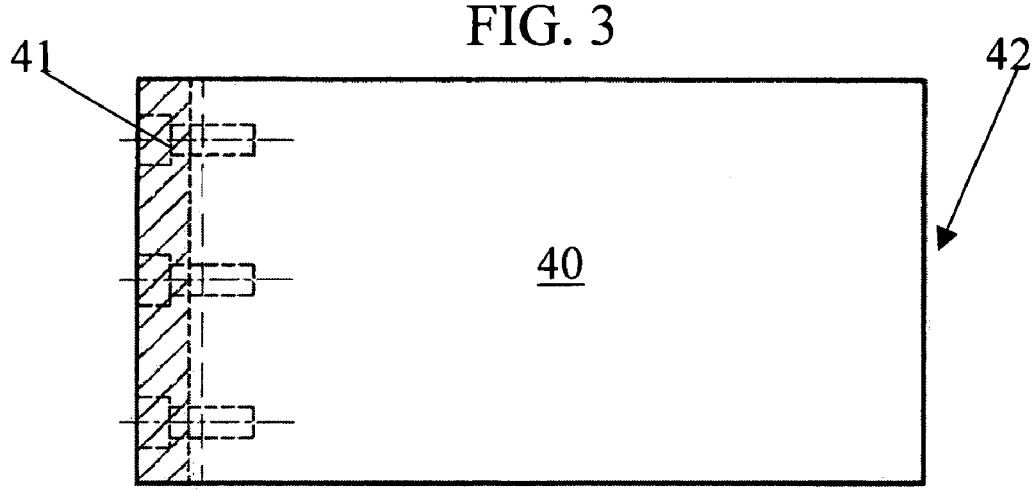
FIG. 4 is a diagram showing a component of the present invention.

FIG. 4 shows the cam 40. Cam assembly bolt 41 secures the top and bottom plate of cam 40. The cam 40 pushes against the follower 23 at a front edge 42 of the cam 40. During testing, the cam 40 provides an equal force of pressure against the follower 23, which is imparted on the specimen 11 via the follower section 22 of the mold 19.

Figure 5:
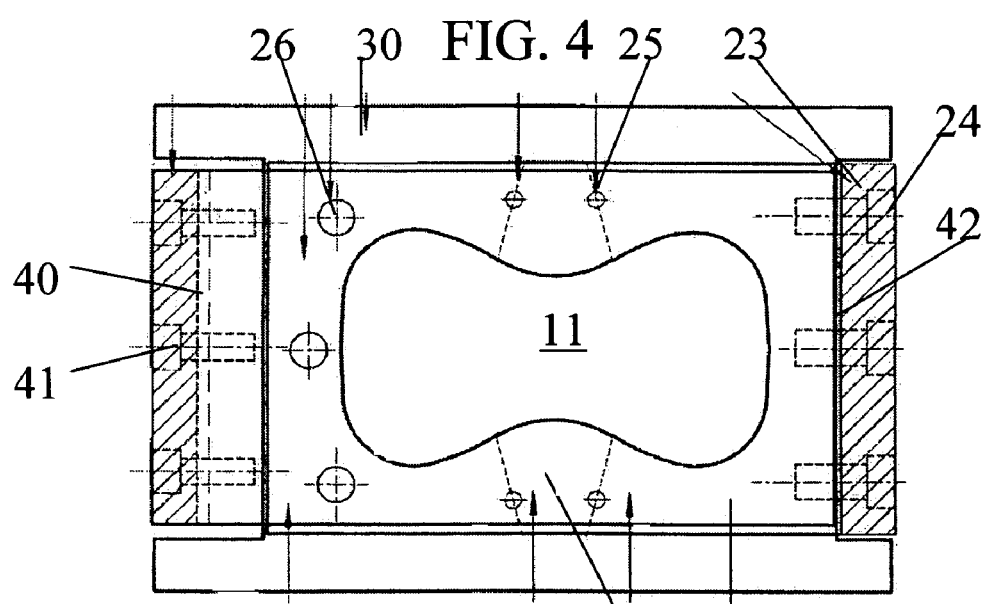
FIG. 5 is top assembly view of an embodiment of the present invention showing the mold body and components.

The fully assembled mold is shown in FIG. 5. The cement specimen 11 is in the mold stationary section 20, the mold floating section 21, and the mold follower section 22. The follower portion 22 is bolted or otherwise attached to the follower 23 at bolt locations 24. Alignment pins 25 align the mold stationary section 20, the mold floating section 21, and the mold follower section 22. Additionally, the mold stationary section 20 is bolted to the mold base 30, shown in FIG. 3 by base bolts 26.

This assembly view shows how the follower 23 can pulls the mold follower section 22 away from the mold stationary section 20 and the mold floating section 21 during testing. The base bolts 26 hold the stationary portion 20 in place as the follower 23 is pushed at the front edge 40 of the cam 40. Cam assembly bolts 41 bolt the cam 40.

Figure 6:
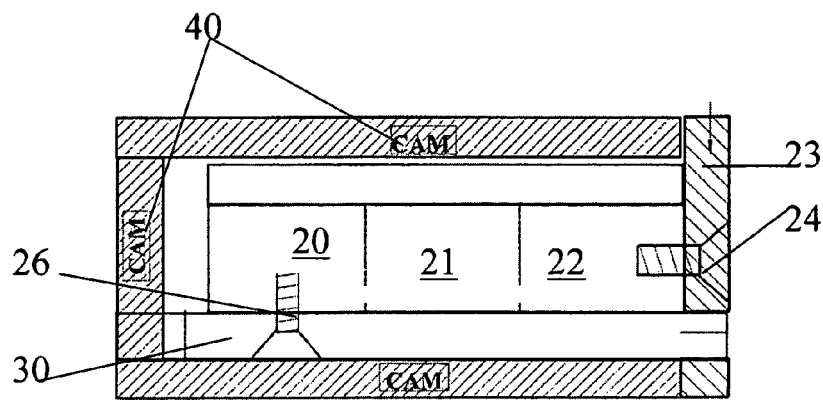
FIG. 6 is a side assembly view of an embodiment of the present invention showing the mold body and components.

This movement is also shown in the side view of the assembly of FIG. 6. The mold stationary section 20, the mold floating section 21, and the mold follower section 22 are shown such that the mold follower section 22 is attached to the follower 23 by bolt 24. The mold stationary section 20 is bolted to the mold base 30 base bolt 26. Cam 40 pushes follower 23, which in turn pulls the mold follower section 22.

Figure 7:
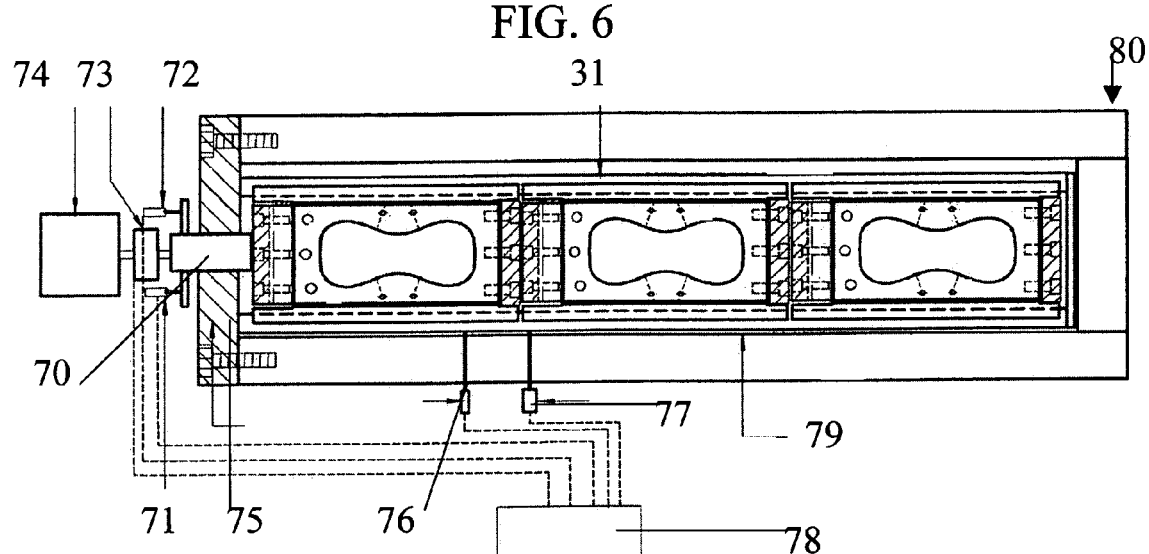
FIG. 7 is top assembly view of another embodiment of the present invention showing a plurality of mold bodies and components.

Turning to FIG. 7, a plurality of testers are shown connected to the railing 31 within a pressure chamber 80, which is used to simulate the temperature and pressure encountered in the wellbore. Piston 70 is disposed through cover 75 of the pressure chamber 80. The piston 70 is moved by a short stroke hydraulic ram 74 or similar device. Precision linear transducers 71, 72 are positioned on opposite sides of the piston 70 to ensure even travel of the piston 70 in to the pressure chamber 80 and to measure the displacement of the cam. A load cell 73 is disposed therein to measure to the amount of force applied by the ram 74.

A thermocouple 76 and a pressure transducer 77 are connected to the pressure chamber 80. Data from the precision linear transducers 71, 72, the thermocouple 76, and the pressure transducer 77 are provided to a data acquisition unit 78.

Those skilled in the art recognize the benefits of this configuration. Cement specimens 11 are placed in molds 30 within the pressure chamber 80. A pressure medium 79, such as fresh water or mineral oil, is introduced to pressurize the system to the temperature and pressure levels that would be encountered in a wellbore environment. The cement specimens 11 are allowed to cure at these temperatures and pressures, as each would under wellbore conditions. Once cured, each specimen 11 is tested using the ram 74 to push the piston 70 such that each specimen 11 is sequentially stressed until failure.

The piston pushes the first cam until the cement specimen 11 fails. The data acquisition unit 78 constantly monitors the precision linear transducers 71, 72, the thermocouple 76, and the pressure transducer 77, collecting data throughout the process. It is important to arrange each mold with enough axial distance such that the failure of each cement specimen will not cause the next follower to be bumped with a breaking force. By axially spacing the cams such that the first specimen fails, the piston ushers the cam forward to smoothly interface with the next cam. The next sample may be stretched in a sequential fashion.

Once the second specimen fails, another axial gap exists such that the rapid expansion of the cams will not strike the third mold. Though three molds are shown in FIG. 7, those skilled in the art will recognize that any plurality of molds within at least one pressure chamber is considered to be within the scope of the invention.

Figure 8:
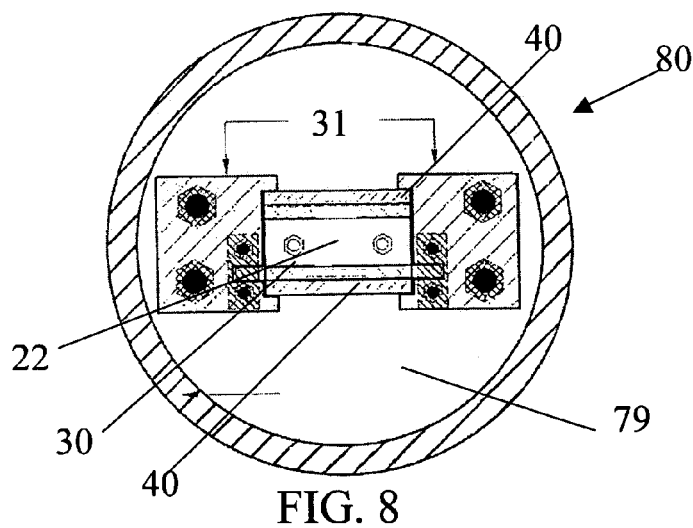
FIG. 8 is a front view of a view of an embodiment of the present invention showing the mold and components in a pressure cylinder.

FIG. 8 shows a cross-sectional view of the pressure chamber 80. The pressurizing medium 79 surrounds the testing apparatus. The rails 31 are connected the mold base 30, wherein the pulled portion of the mold 22 is shown on top of the mold base 30. The cam 40 is shown above and below the mold base 30. This arrangement shows how the cam 40 urges the pulled portion of the mold 22 toward the viewer, thus stressing the cement specimen in the mold until failure.

EXAMPLES

Three cement specimens were cured at atmospheric pressure, 198° F., and 20.0 ppg. The slurry design was used for this experiment was primarily Norcem AS G with 45% W-10+20% MPA-3+0.01797 gps CD-31L+0.0839 pgs R-15L+0.02 gps FP-6L. A maximum cycle load of 5000 N (2027 psi) was applied.

Figure 9:
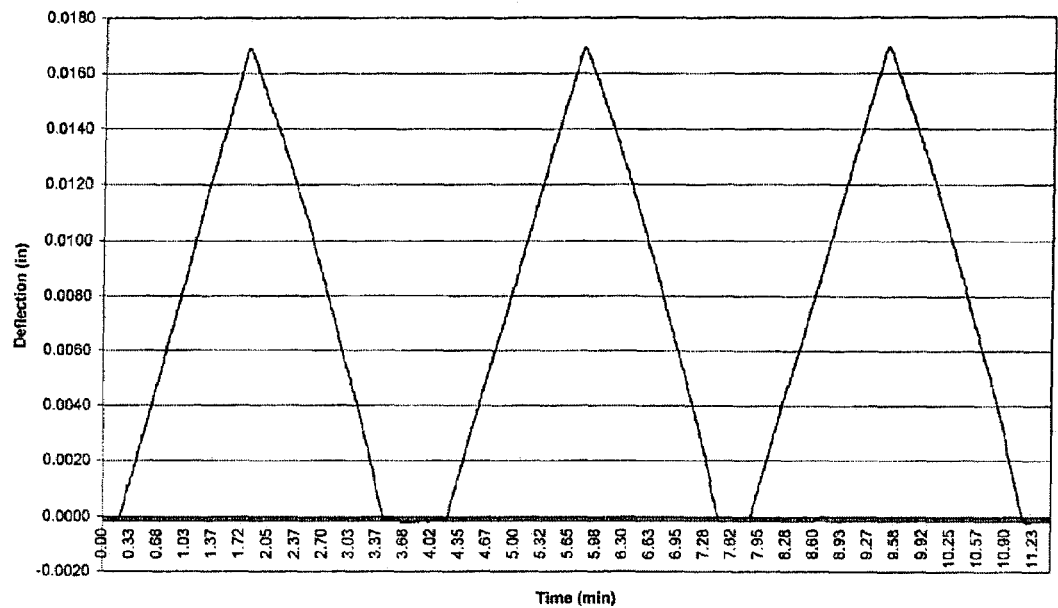
FIG. 9 is a representative graph showing deflection versus time.

The deflection versus time graph in FIG. 9 shows the consistency of the deflection of the samples prior to failure. The peaks of the graphs are very similar and the time to failure of the three samples has a similar width on the X-axis.

Figure 10:
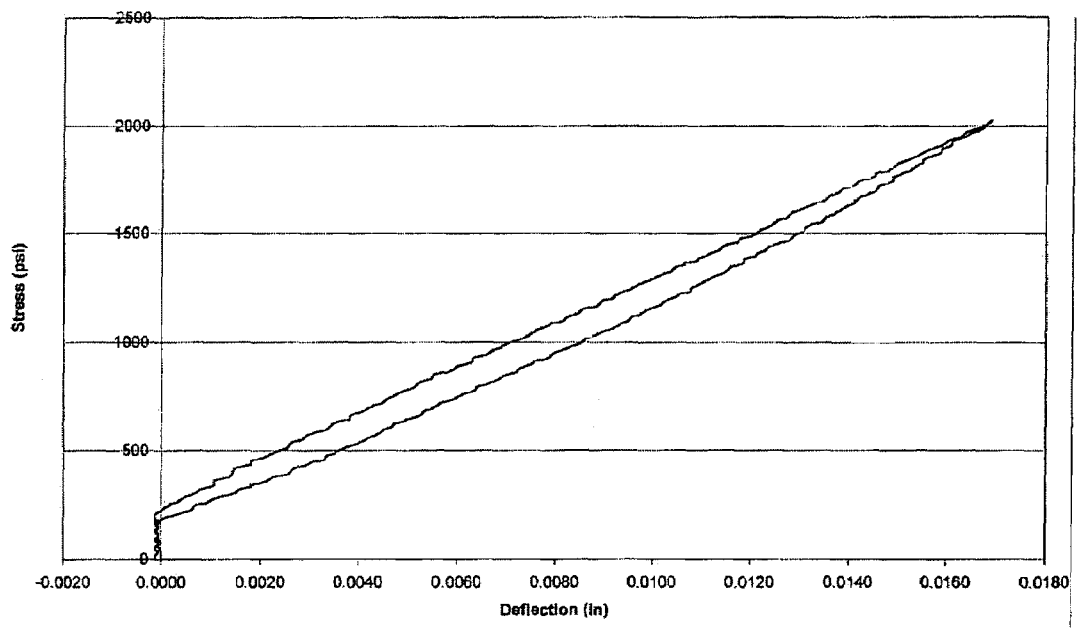
FIG. 10 is a representative graph showing stress versus deflection.

FIG. 10 shows the flexural stress (psi) versus the deflection (inches) for one of these samples. The linear increase of deflection as the stress increased shows the consistency of the results. When the deflection is compared to the Young's Modulus, as shown in FIG. 11, the graph shows the flattening the Young's modulus as the sample's deflection nears the failure point.

Figure 11:
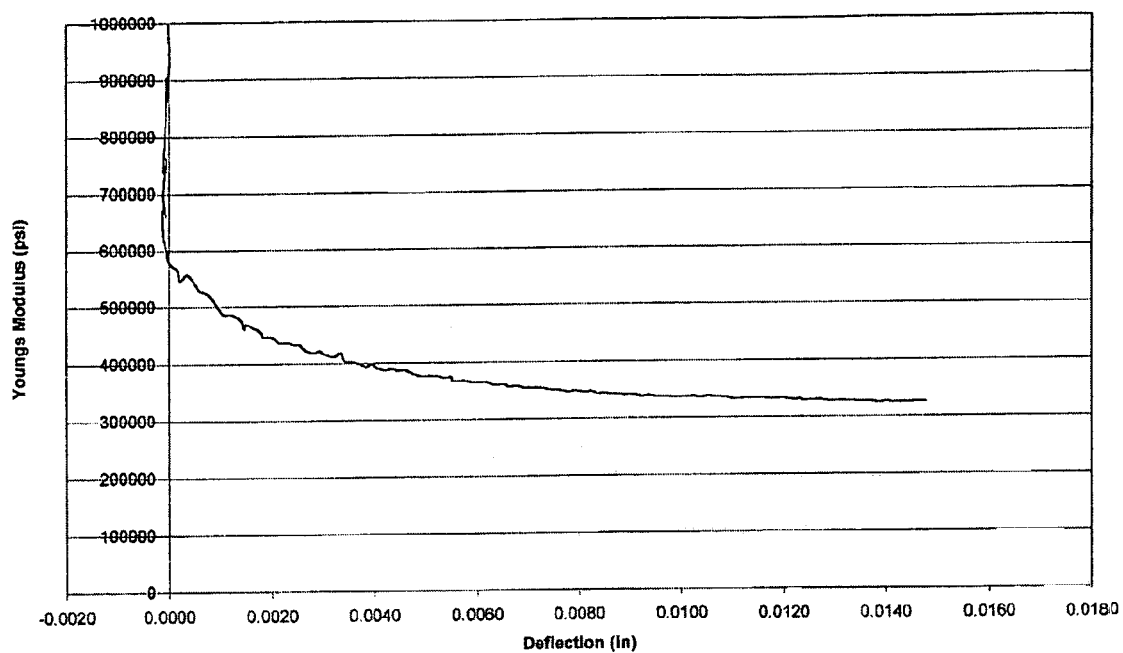
FIG. 11 is a representative graph showing Young's Modulus versus deflection.
Figure 12:
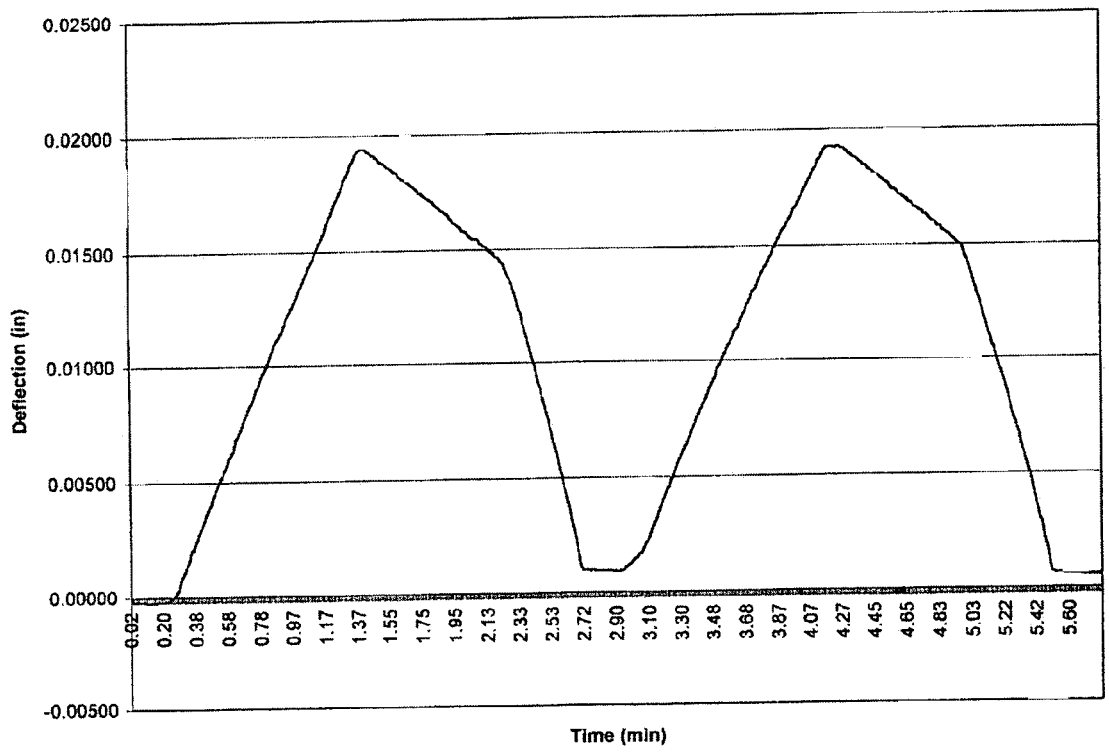
FIG. 12 is a representative graph showing deflection versus time.
Figure 13:
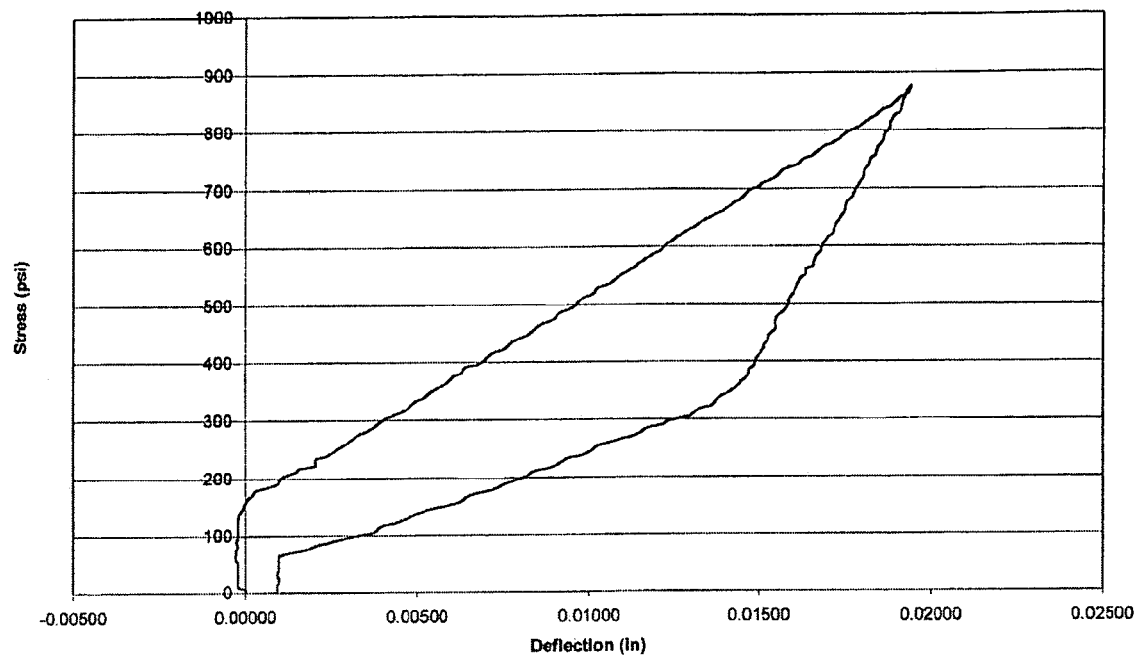
FIG. 13 is a representative graph showing stress versus deflection.
Figure 14:
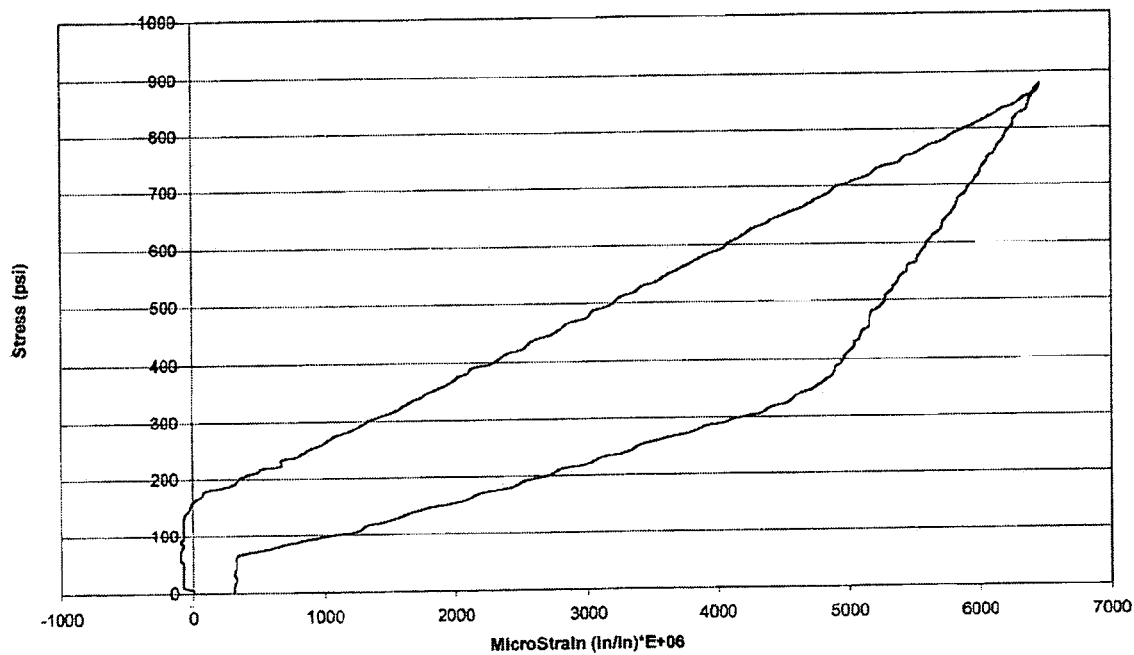
FIG. 14 is a representative graph showing stress versus microstrain.

Two additional samples are shown in FIG. 11 in a tensile strength test. Using the same slurry, a maximum cycle load of 3900 N (878 psi) with an actual failure load of 4725 N (1064 psi) was applied. Again, the consistency of the shape of the peaks and width of the results on the X-axis show the preciseness of the tester in this analysis. The graph in FIG. 12 shows the tensile stress versus the deflection of the sample under tension only. This is in comparison with FIG. 13 that shows the tensile strength test of the stress versus the microstrain.

In another experiment, Calport H cement was mixed at 16.5 ppg and cured for about 48 hours at atmospheric temperature and pressure. The following table depicts the three specimens as stress using the above-disclosed tester was applied on each specimen. The deflection was measured using the precision linear transducers listed above.

TABLE 1

| | Calport H Stress v. Deflection Testing | | | | | |
|---|---|---|---|---|---|---|
| Time (sec) | Deflect 1 (inches) | Stress 1 (psi) | Deflect 2 (inches) | Stress 2 (psi) | Deflect 3 (inches) | Stress 3 (psi) |
| 0 | 0 | 0 | 0 | 0 | 0 | 0 |
| 1.002 | 0 | 0 | 0 | 0 | 0 | 0 |
| 1.998 | 0 | 0 | 0 | 0 | 0 | −5.775096 |
| 3.000 | 0 | 0 | 0 | 0 | 0 | 0 |
| 4.002 | 0 | 0 | 0 | 0 | 0 | 0 |

TABLE 1-continued

Calport H Stress v. Deflection Testing

| Time (sec) | Deflect 1 (inches) | Stress 1 (psi) | Deflect 2 (inches) | Stress 2 (psi) | Deflect 3 (inches) | Stress 3 (psi) |
|---|---|---|---|---|---|---|
| 4.998 | 0 | 0 | 0 | 0 | 0 | 0 |
| 6.000 | 0 | 0 | 0 | 0 | 0 | 5.775096 |
| 7.000 | 0 | 5.775096 | 0 | 11.550184 | 0 | 5.775096 |
| 8.000 | 0 | 5.775096 | 0 | 11.550184 | 0 | 11.550184 |
| 9.000 | 0 | 11.550192 | 0 | 11.550184 | 0 | 11.550184 |
| 10.000 | 0 | 17.32528 | 0 | 17.32528 | 0 | 17.32528 |
| 11.000 | 0 | 17.32528 | 0 | 17.32528 | 0 | 17.32528 |
| 12.000 | 0 | 23.100376 | 0 | 23.100376 | 0 | 23.100376 |
| 13.000 | 0 | 23.100376 | 0 | 28.875464 | 0.0001 | 28.875472 |
| 14.000 | 0 | 28.875472 | 0 | 28.875464 | 0 | 28.875472 |
| 15.000 | 0 | 28.875472 | 0 | 28.875464 | 0.0001 | 28.875472 |
| 16.000 | 0 | 28.875472 | 0 | 34.6505616 | 0.0001 | 34.65056 |
| 17.000 | 0 | 34.650568 | 0 | 34.6505616 | 0.0001 | 34.65056 |
| 18.000 | 0 | 34.650568 | 0 | 40.425656 | 0.0001 | 34.65056 |
| 19.000 | 0 | 34.650568 | 0 | 40.425656 | 0.0001 | 34.65056 |
| 20.000 | 0 | 40.425656 | 0 | 40.425656 | 0.0001 | 40.4256576 |
| 21.000 | 0 | 40.425656 | 0 | 46.2007504 | 0.0001 | 46.200752 |
| 22.000 | 0 | 40.425656 | 0 | 46.2007504 | 0.0001 | 46.200752 |
| 23.000 | 0 | 46.2007536 | 0.0001 | 51.975848 | 0.0001 | 51.9758464 |
| 24.000 | 0.0001 | 46.2007536 | 0.0001 | 51.975848 | 0.0001 | 57.750944 |
| 25.000 | 0.0001 | 51.975848 | 0.0001 | 57.750936 | 0.0001 | 57.750944 |
| 26.000 | 0.0001 | 51.975848 | 0.0001 | 57.750936 | 0.0005 | 63.526032 |
| 27.000 | 0.0001 | 57.7509424 | 0.0001 | 63.526032 | 0.0006 | 69.301128 |
| 28.000 | 0.0001 | 57.7509424 | 0.0001 | 63.526032 | 0.0008 | 69.301128 |
| 29.000 | 0.0001 | 63.52604 | 0.0004 | 63.526032 | 0.0009 | 69.301128 |
| 30.000 | 0.0001 | 63.52604 | 0.0004 | 69.301128 | 0.001 | 75.076224 |
| 31.000 | 0.0001 | 69.301128 | 0.0005 | 69.301128 | 0.0012 | 75.076224 |
| 32.000 | 0.0001 | 75.076224 | 0.0006 | 75.076224 | 0.0013 | 80.85132 |
| 33.000 | 0.0001 | 75.076224 | 0.0007 | 75.076224 | 0.0014 | 80.85132 |
| 34.000 | 0.0004 | 75.076224 | 0.0008 | 80.851312 | 0.0016 | 86.626408 |
| 35.000 | 0.0004 | 75.076224 | 0.0009 | 86.626408 | 0.0017 | 92.401504 |
| 36.000 | 0.0005 | 80.85132 | 0.001 | 92.401504 | 0.0018 | 92.401504 |
| 37.000 | 0.0006 | 80.85132 | 0.0011 | 92.401504 | 0.002 | 98.1766 |
| 38.000 | 0.0007 | 86.626416 | 0.0013 | 92.401504 | 0.0021 | 98.1766 |
| 39.000 | 0.0008 | 92.401504 | 0.0013 | 98.1766 | 0.0023 | 103.951696 |
| 40.000 | 0.001 | 92.401504 | 0.0015 | 98.1766 | 0.0024 | 103.951696 |
| 41.000 | 0.001 | 98.1766 | 0.0015 | 103.951696 | 0.0025 | 103.951696 |
| 42.000 | 0.0012 | 103.951696 | 0.0017 | 103.951696 | 0.0026 | 109.726792 |
| 43.000 | 0.0013 | 103.951696 | 0.0017 | 109.726784 | 0.0027 | 115.50188 |
| 44.000 | 0.0013 | 103.951696 | 0.0019 | 109.726784 | 0.0029 | 115.50188 |
| 45.000 | 0.0015 | 109.726792 | 0.0019 | 115.50188 | 0.003 | 121.276976 |
| 46.000 | 0.0016 | 109.726792 | 0.0021 | 115.50188 | 0.0031 | 121.276976 |
| 47.000 | 0.0017 | 115.501888 | 0.0021 | 121.276984 | 0.0033 | 121.276976 |
| 48.000 | 0.0019 | 121.276976 | 0.0022 | 121.276984 | 0.0034 | 127.05208 |
| 49.000 | 0.002 | 121.276976 | 0.0024 | 127.052104 | 0.0035 | 127.05208 |
| 50.000 | 0.0021 | 127.052072 | 0.0024 | 132.827144 | 0.0037 | 138.60224 |
| 51.000 | 0.0022 | 127.052072 | 0.0026 | 132.827144 | 0.0038 | 138.60224 |
| 52.000 | 0.0023 | 127.052072 | 0.0027 | 132.827144 | 0.004 | 138.60224 |
| 53.000 | 0.0025 | 132.827176 | 0.0028 | 138.602264 | 0.0041 | 138.60224 |
| 54.000 | 0.0025 | 132.827176 | 0.0029 | 138.602264 | 0.0042 | 144.37736 |
| 55.000 | 0.0027 | 144.377336 | 0.0031 | 144.377384 | 0.0043 | 150.15248 |
| 56.000 | 0.0028 | 144.377336 | 0.0031 | 150.152424 | 0.0044 | 155.92752 |
| 57.000 | 0.003 | 144.377336 | 0.0033 | 150.152424 | 0.0045 | 155.92752 |
| 58.000 | 0.0031 | 144.377336 | 0.0034 | 150.152424 | 0.0047 | 155.92752 |
| 59.000 | 0.0031 | 150.152456 | 0.0036 | 155.927544 | | |
| 60.000 | 0.0033 | 155.927576 | 0.0036 | 155.927544 | | |
| 61.000 | | | 0.0038 | 161.702664 | | |
| 62.000 | | | 0.0039 | 161.702664 | | |
| 63.000 | | | 0.0041 | 167.477704 | | |
| 64.000 | | | 0.0042 | 167.477704 | | |

Figure 15:
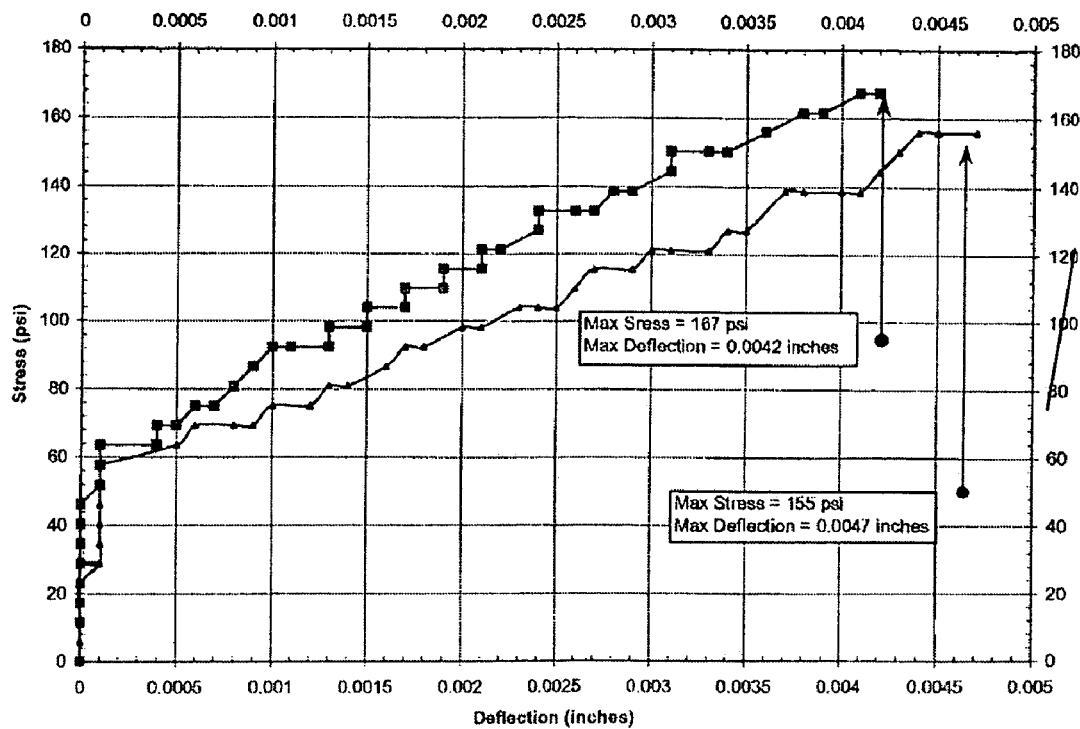
FIG. 15 is a representative graph showing stress versus deflection.

As shown in this table, the first and third specimens bear similar results, namely 155.927 psi with 0.0033 inches deflection and 0.0047 inches deflection, respectively while the second specimen bears 167.478 psi and 0.0042 inches deflection. The data for the second and third specimens have been graphed in FIG. 15. The closeness of this data indicates the consistency of the testing technique. It is envisioned that this consistency will be seen in pressurized experiments.

In another experiment, Calport G cement was mixed at 15.8 ppg and cured for about 48 hrs at 130° F. and atmospheric pressure. Two specimens were tested:

TABLE 2

Calport G Stress v. Deflection Testing

| Time (sec) | Deflect 2 (inches) | Stress 2 (psi) | Deflect 1 | Stress 1 (psi) |
|---|---|---|---|---|
| 1 | 0 | 21.787232 | 0 | 21.787232 |
| 2 | 0 | 21.787232 | 0 | 21.787232 |
| 3 | 0 | 21.787232 | 0 | 21.787232 |
| 4 | 0 | 21.787232 | 0 | 21.787232 |
| 5 | 0 | 21.787232 | 0 | 21.787232 |
| 6 | 0 | 21.787232 | 0 | 21.787232 |
| 7 | 0 | 21.787232 | 0 | 21.787232 |
| 8 | 0 | 21.787232 | 0 | 21.787232 |
| 9 | 0 | 21.787232 | 0 | 21.787232 |
| 10 | 0 | 27.23404 | 0 | 21.787232 |
| 11 | 0 | 32.680856 | 0 | 27.23404 |
| 12 | 0 | 32.680856 | 0 | 27.23404 |
| 13 | 0 | 38.127664 | 0 | 32.680856 |
| 14 | 0 | 43.574472 | 0 | 38.127664 |
| 15 | 0 | 43.574472 | 0 | 38.127664 |
| 16 | 0 | 43.574472 | 0 | 43.574472 |
| 17 | 0 | 49.02128 | 0 | 43.574472 |
| 18 | 0 | 49.02128 | 0 | 43.574472 |
| 19 | 0 | 49.02128 | 0 | 43.574472 |
| 20 | 0 | 54.468088 | 0 | 49.02128 |
| 21 | 0 | 59.914896 | 0 | 54.468088 |
| 22 | 0 | 59.914896 | 0 | 54.468088 |
| 23 | 0 | 59.914896 | 0 | 59.914896 |
| 24 | 0 | 65.361704 | 0 | 59.914896 |
| 25 | 0 | 65.361704 | 0 | 59.914896 |
| 26 | 0 | 70.808512 | 0 | 65.361704 |
| 27 | 0 | 70.808512 | 0 | 65.361704 |
| 28 | 0 | 76.25532 | 0 | 70.808512 |
| 29 | 0 | 76.25532 | 0 | 70.808512 |
| 30 | 0 | 81.70216 | 0 | 76.25532 |
| 31 | 0 | 81.70216 | 0 | 76.25532 |
| 32 | 0 | 81.70216 | 0 | 81.70216 |
| 33 | 0 | 87.14896 | 0 | 81.70216 |
| 34 | 0 | 87.14896 | 0 | 87.14896 |
| 35 | 0 | 92.59576 | 0 | 87.14896 |
| 36 | 0 | 98.04256 | 0 | 92.59576 |
| 37 | 0 | 98.04256 | 0 | 92.59576 |
| 38 | 0 | 98.04256 | 0 | 98.04256 |
| 39 | 0 | 103.48936 | 0 | 98.04256 |
| 40 | 0 | 103.48936 | 0 | 98.04256 |
| 41 | 0 | 108.93616 | 0 | 98.04256 |
| 42 | 0.0001 | 108.93616 | 0 | 103.48936 |
| 43 | 0.0001 | 114.38296 | 0 | 103.48936 |
| 44 | 0.0001 | 114.38296 | 0 | 108.93616 |
| 45 | 0.0001 | 119.82976 | 0 | 108.93616 |
| 46 | 0.0001 | 119.82976 | 0 | 114.38296 |
| 47 | 0.0001 | 125.27656 | 0 | 114.38296 |
| 48 | 0.0001 | 125.27656 | 0 | 119.82976 |
| 49 | 0.0004 | 130.72344 | 0 | 119.82976 |
| 50 | 0.0005 | 136.17024 | 0 | 119.82976 |
| 51 | 0.0005 | 136.17024 | 0 | 125.27656 |
| 52 | 0.0005 | 136.17024 | 0 | 125.27656 |
| 53 | 0.0006 | 141.61704 | 0.0001 | 130.72344 |
| 54 | 0.0007 | 147.06384 | 0.0001 | 136.17024 |
| 55 | 0.0007 | 147.06384 | 0.0001 | 136.17024 |
| 56 | 0.0008 | 152.51064 | 0.0001 | 141.61704 |
| 57 | 0.0009 | 152.51064 | 0.0009 | 147.06384 |
| 58 | 0.0009 | 157.95744 | 0.001 | 147.06384 |
| 59 | 0.001 | 157.95744 | 0.001 | 152.51064 |
| 60 | 0.001 | 163.40424 | 0.001 | 152.51064 |

TABLE 2-continued

Calport G Stress v. Deflection Testing

| Time (sec) | Deflect 2 (inches) | Stress 2 (psi) | Deflect 1 | Stress 1 (psi) |
|---|---|---|---|---|
| 61 | 0.0011 | 163.40424 | 0.001 | 152.51064 |
| 62 | 0.0011 | 168.85104 | 0.001 | 157.95744 |
| 63 | 0.0012 | 168.85104 | 0.001 | 157.95744 |
| 64 | 0.0013 | 174.29784 | 0.001 | 163.40424 |
| 65 | 0.0013 | 174.29784 | 0.0013 | 163.40424 |
| 66 | 0.0014 | 179.74472 | 0.0013 | 168.85104 |
| 67 | 0.0015 | 179.74472 | 0.0013 | 174.29784 |
| 68 | 0.0016 | 185.19152 | 0.0013 | 174.29784 |
| 69 | 0.0017 | 185.19152 | 0.0014 | 174.29784 |
| 70 | 0.0017 | 185.19152 | 0.0014 | 179.74472 |
| 71 | 0.0018 | 185.19152 | 0.0015 | 185.19152 |
| 72 | 0.0019 | 190.63832 | 0.0015 | 185.19152 |
| 73 | 0.0019 | 190.63832 | 0.0016 | 185.19152 |
| 74 | 0.002 | 196.08512 | 0.0016 | 185.19152 |
| 75 | 0.0021 | 196.08512 | 0.0017 | 185.19152 |
| 76 | 0.0022 | 201.53192 | 0.0017 | 190.63832 |
| 77 | 0.0023 | 201.53192 | 0.0018 | 196.08512 |
| 78 | 0.0023 | 206.97872 | 0.0019 | 196.08512 |
| 79 | 0.0024 | 206.97872 | 0.002 | 201.53192 |
| 80 | 0.0025 | 212.42552 | 0.002 | 201.53192 |
| 81 | 0.0026 | 212.42552 | 0.0021 | 201.53192 |
| 82 | 0.0027 | 212.42552 | 0.0022 | 206.97872 |
| 83 | 0.0028 | 217.87232 | 0.0022 | 212.42552 |
| 84 | 0.0028 | 217.87232 | 0.0023 | 212.42552 |
| 85 | 0.0029 | 223.3192 | 0.0023 | 212.42552 |
| 86 | 0.003 | 223.3192 | 0.0025 | 217.87232 |
| 87 | 0.0031 | 228.766 | 0.0025 | 217.87232 |
| 88 | 0.0032 | 228.766 | 0.0026 | 223.3192 |
| 89 | 0.0032 | 228.766 | 0.0027 | 223.3192 |
| 90 | 0.0033 | 234.2128 | 0.0027 | 223.3192 |
| 91 | 0.0034 | 234.2128 | 0.0028 | 228.766 |
| 92 | 0.0035 | 239.6596 | 0.0029 | 228.766 |
| 93 | 0.0036 | 239.6596 | 0.003 | 234.2128 |
| 94 | 0.0037 | 239.6596 | 0.0031 | 234.2128 |
| 95 | 0.0038 | 245.1064 | 0.0032 | 239.6596 |
| 96 | 0.0039 | 250.5532 | 0.0032 | 239.6596 |
| 97 | 0.0039 | 250.5532 | 0.0033 | 239.6596 |
| 98 | 0.0041 | 250.5532 | 0.0034 | 245.1064 |
| 99 | 0.0041 | 256 | 0.0035 | 250.5532 |
| 100 | 0.0042 | 256 | 0.0036 | 250.5532 |
| 101 | 0.0043 | 256 | 0.0037 | 250.5532 |
| 102 | 0.0044 | 261.4468 | 0.0038 | 256 |
| 103 | 0.0045 | 261.4468 | 0.0039 | 256 |
| 104 | 0.0046 | 266.8936 | 0.004 | 261.4468 |
| 105 | 0.0047 | 266.8936 | 0.004 | 261.4468 |
| 106 | 0.0048 | 266.8936 | 0.0042 | 266.8936 |
| 107 | 0.0049 | 272.3404 | 0.0042 | 266.8936 |
| 108 | 0.005 | 272.3404 | 0.0044 | 266.8936 |
| 109 | 0.0051 | 277.7872 | 0.0044 | 272.3404 |
| 110 | 0.0052 | 277.7872 | 0.0046 | 272.3404 |
| 111 | 0.0053 | 277.7872 | 0.0046 | 272.3404 |
| 112 | 0.0054 | 283.23408 | 0.0047 | 277.7872 |
| 113 | 0.0055 | 283.23408 | 0.0048 | 277.7872 |
| 114 | 0.0056 | 288.68088 | 0.0049 | 283.23408 |
| 115 | 0.0057 | 288.68088 | 0.005 | 283.23408 |
| 116 | 0.0058 | 294.12768 | 0.0051 | 288.68088 |
| 117 | 0.0059 | 294.12768 | 0.0052 | 288.68088 |
| 118 | 0.006 | 294.12768 | 0.0053 | 294.12768 |
| 119 | 0.0061 | 294.12768 | 0.0054 | 294.12768 |
| 120 | 0.0062 | 299.57448 | 0.0055 | 294.12768 |
| 121 | 0.0063 | 305.02128 | 0.0056 | 299.57448 |
| 122 | 0.0064 | 305.02128 | 0.0058 | 299.57448 |
| 123 | 0.0065 | 305.02128 | 0.0058 | 305.02128 |
| 124 | 0.0066 | 310.46808 | 0.006 | 305.02128 |
| 125 | 0.0067 | 310.46808 | 0.006 | 305.02128 |
| 126 | 0.0068 | 315.91488 | 0.0062 | 310.46808 |
| 127 | 0.0069 | 315.91488 | 0.0062 | 310.46808 |
| 128 | 0.007 | 315.91488 | 0.0064 | 315.91488 |
| 129 | 0.0071 | 321.36168 | 0.0064 | 315.91488 |
| 130 | 0.0072 | 326.80856 | 0.0067 | 315.91488 |
| 131 | 0.0073 | 326.80856 | 0.0067 | 321.36168 |
| 132 | 0.0074 | 326.80856 | 0.0069 | 326.80856 |
| 133 | 0.0075 | 326.80856 | 0.007 | 326.80856 |
| 134 | 0.0076 | 332.25536 | 0.0072 | 326.80856 |

TABLE 2-continued

Calport G Stress v. Deflection Testing

| Time (sec) | Deflect 2 (inches) | Stress 2 (psi) | Deflect 1 | Stress 1 (psi) |
|---|---|---|---|---|
| 135 | 0.0077 | 332.25536 | 0.0073 | 332.25536 |
| 136 | 0.0078 | 332.25536 | 0.0074 | 332.25536 |
| 137 | 0.0079 | 337.70216 | 0.0075 | 332.25536 |
| 138 | 0.008 | 343.14896 | 0.0076 | 337.70216 |
| 139 | 0.0081 | 343.14896 | 0.0078 | 337.70216 |
| 140 | 0.0082 | 348.59576 | 0.0079 | 343.14896 |
| 141 | 0.0083 | 348.59576 | 0.0081 | 348.59576 |
| 142 | 0.0084 | 348.59576 | 0.0083 | 348.59576 |
| 143 | 0.0086 | 348.59576 | 0.0085 | 348.59576 |
| 144 | 0.0087 | 348.59576 | 0.0086 | 348.59576 |
| 145 | 0.0088 | 348.59576 | 0.0088 | 348.59576 |
| 146 | 0.0089 | 348.59576 | 0.0093 | 348.59576 |
| 147 | 0.0091 | 354.04256 | 0.0093 | 348.59576 |
| 148 | 0.0092 | 359.48936 | 0.0097 | 354.04256 |
| 149 | 0.0093 | 359.48936 | 0.0098 | 354.04256 |
| 150 | 0.0094 | 364.93616 | 0.0102 | 359.48936 |
| 151 | 0.0096 | 364.93616 | 0.0104 | 359.48936 |
| 152 | 0.0097 | 364.93616 | 0.0107 | 364.93616 |
| 153 | 0.0098 | 370.38296 | 0.0111 | 364.93616 |
| 154 | 0.0099 | 370.38296 | 0.0114 | 364.93616 |
| 155 | 0.0101 | 370.38296 | 0.0119 | 364.93616 |
| 156 | 0.0102 | 375.82976 | 0.0125 | 370.38296 |
| 157 | 0.0103 | 375.82976 | 0.0126 | 370.38296 |
| 158 | 0.0104 | 381.27664 | 0.0134 | 370.38296 |
| 159 | 0.0106 | 381.27664 | 0.0136 | 375.82976 |
| 160 | 0.0107 | 386.72344 | 0.0142 | 381.27664 |
| 161 | 0.0109 | 386.72344 | 0.0146 | 381.27664 |
| 162 | 0.011 | 386.72344 | | |
| 163 | 0.0111 | 392.17024 | | |
| 164 | 0.0113 | 392.17024 | | |
| 165 | 0.0114 | 392.17024 | | |
| 166 | 0.0115 | 397.61704 | | |
| 167 | 0.0116 | 397.61704 | | |
| 168 | 0.0118 | 397.61704 | | |
| 169 | 0.0119 | 403.06384 | | |
| 170 | 0.012 | 403.06384 | | |
| 171 | 0.0121 | 408.51064 | | |
| 172 | 0.0122 | 408.51064 | | |
| 173 | 0.0124 | 408.51064 | | |
| 174 | 0.0125 | 413.95744 | | |
| 175 | 0.0126 | 413.95744 | | |
| 176 | 0.0126 | 419.40424 | | |
| 177 | 0.0128 | 419.40424 | | |
| 178 | 0.0129 | 419.40424 | | |
| 179 | 0.013 | 424.85104 | | |
| 180 | 0.0131 | 424.85104 | | |
| 181 | 0.0132 | 430.29792 | | |
| 182 | 0.0133 | 430.29792 | | |
| 183 | 0.0134 | 430.29792 | | |
| 184 | 0.0135 | 430.29792 | | |
| 185 | 0.0136 | 435.74464 | | |

Figure 16:
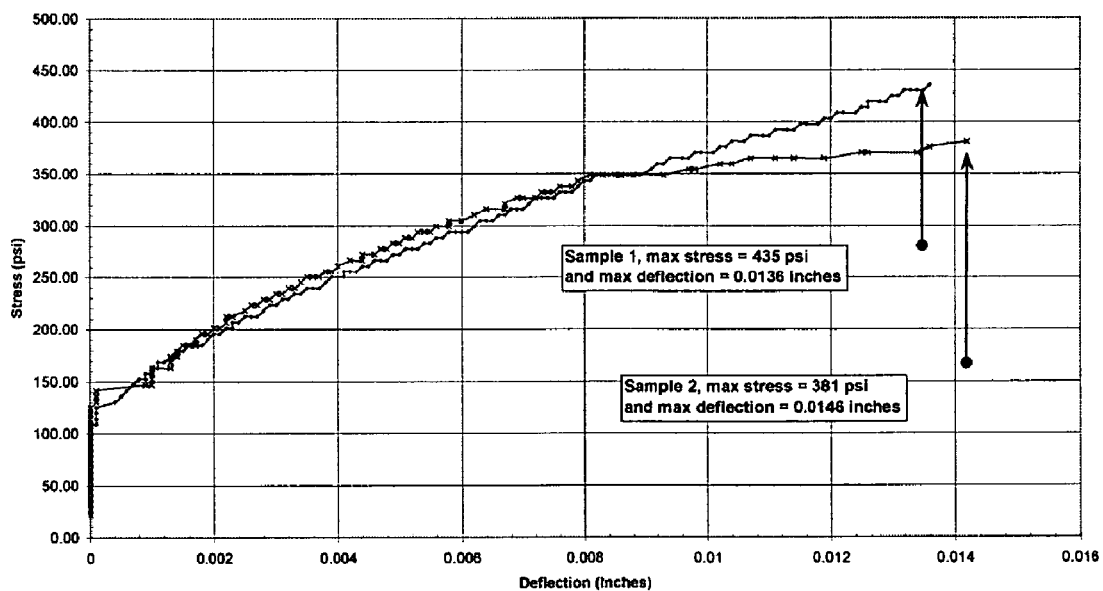
FIG. 16 is a representative graph showing stress versus deflection.

As shown in this table, the first specimen bore 381.276 psi and 0.0146 inches deflection while the second specimen boar 435.745 psi and 0.0136 inches deflection. The data for the first and second specimens have been graphed in FIG. 16. The closeness of this data indicates the consistency of the testing technique. It is envisioned that this consistency will be seen in pressurized experiments.

In another experiment, Calport G cement was mixed at 15.8 ppg and cured for about 48 hours at 130° F. and atmospheric pressure. Two specimens were tested.

TABLE 3

Second Calport G Stress v. Deflection Testing

| Time (sec) | Deflection 2 (inches) | Stress 2 (psi) | Deflection 1 (inches) | Stress 1 (psi) |
|---|---|---|---|---|
| 0 | 0.000 | 10.894 | 0.0000 | 21.79 |
| 1.000 | 0.000 | 10.894 | 0.0000 | 21.79 |
| 2.000 | 0.000 | 10.894 | 0.0000 | 21.79 |
| 3.000 | 0.000 | 16.340 | 0.0000 | 21.79 |
| 4.000 | 0.000 | 16.340 | 0.0000 | 21.79 |
| 5.000 | 0.000 | 16.340 | 0.0000 | 21.79 |
| 6.000 | 0.000 | 16.340 | 0.0000 | 21.79 |
| 7.000 | 0.000 | 21.787 | 0.0000 | 27.23 |
| 8.000 | 0.000 | 21.787 | 0.0000 | 27.23 |
| 9.000 | 0.000 | 21.787 | 0.0000 | 32.68 |
| 10.000 | 0.000 | 21.787 | 0.0000 | 38.13 |
| 11.000 | 0.000 | 27.234 | 0.0000 | 38.13 |
| 12.000 | 0.000 | 27.234 | 0.0000 | 43.57 |
| 13.000 | 0.000 | 27.234 | 0.0000 | 49.02 |
| 14.000 | 0.000 | 32.681 | 0.0000 | 49.02 |
| 15.000 | 0.000 | 38.128 | 0.0000 | 49.02 |
| 16.000 | 0.000 | 38.128 | 0.0000 | 54.47 |
| 17.000 | 0.001 | 43.574 | 0.0000 | 54.47 |
| 18.000 | 0.001 | 43.574 | 0.0000 | 59.91 |
| 19.000 | 0.001 | 49.021 | 0.0000 | 59.91 |
| 20.000 | 0.001 | 54.468 | 0.0000 | 59.91 |
| 21.000 | 0.001 | 59.915 | 0.0000 | 59.91 |
| 22.000 | 0.001 | 59.915 | 0.0000 | 65.36 |
| 23.000 | 0.001 | 65.362 | 0.0000 | 70.81 |
| 24.000 | 0.001 | 70.809 | 0.0000 | 76.26 |
| 25.000 | 0.001 | 70.809 | 0.0000 | 76.26 |
| 26.000 | 0.001 | 76.255 | 0.0000 | 76.26 |
| 27.000 | 0.001 | 81.702 | 0.0001 | 76.26 |
| 28.000 | 0.001 | 81.702 | 0.0001 | 81.70 |
| 29.000 | 0.001 | 81.702 | 0.0001 | 87.15 |
| 30.000 | 0.001 | 87.149 | 0.0001 | 87.15 |
| 31.000 | 0.001 | 87.149 | 0.0001 | 87.15 |
| 32.000 | 0.001 | 92.596 | 0.0001 | 92.60 |
| 33.000 | 0.001 | 98.043 | 0.0001 | 98.04 |
| 34.000 | 0.002 | 98.043 | 0.0001 | 98.04 |
| 35.000 | 0.002 | 103.489 | 0.0001 | 98.04 |
| 36.000 | 0.002 | 103.489 | 0.0001 | 98.04 |
| 37.000 | 0.002 | 108.936 | 0.0001 | 103.49 |
| 38.000 | 0.002 | 114.383 | 0.0001 | 108.94 |
| 39.000 | 0.002 | 114.383 | 0.0003 | 114.38 |
| 40.000 | 0.002 | 119.830 | 0.0004 | 114.38 |
| 41.000 | 0.002 | 119.830 | 0.0005 | 114.38 |
| 42.000 | 0.002 | 119.830 | 0.0006 | 119.83 |
| 43.000 | 0.002 | 119.830 | 0.0006 | 119.83 |
| 44.000 | 0.002 | 125.277 | 0.0007 | 125.28 |
| 45.000 | 0.002 | 130.723 | 0.0007 | 125.28 |
| 46.000 | 0.002 | 130.723 | 0.0008 | 136.17 |
| 47.000 | 0.002 | 136.170 | 0.0008 | 136.17 |
| 48.000 | 0.002 | 136.170 | 0.0009 | 136.17 |
| 49.000 | 0.002 | 141.617 | 0.0010 | 136.17 |
| 50.000 | 0.003 | 141.617 | 0.0011 | 136.17 |
| 51.000 | 0.003 | 147.064 | 0.0012 | 136.17 |
| 52.000 | 0.003 | 147.064 | 0.0013 | 147.06 |
| 53.000 | 0.003 | 152.511 | 0.0014 | 147.06 |
| 54.000 | 0.003 | 152.511 | 0.0015 | 152.51 |
| 55.000 | 0.003 | 152.511 | 0.0016 | 152.51 |
| 56.000 | 0.003 | 157.957 | 0.0017 | 157.96 |
| 57.000 | 0.003 | 157.957 | 0.0018 | 157.96 |
| 58.000 | 0.003 | 163.404 | 0.0019 | 163.40 |
| 59.000 | 0.003 | 163.404 | 0.0020 | 163.40 |
| 60.000 | 0.003 | 168.851 | 0.0021 | 168.85 |
| 61.000 | 0.003 | 168.851 | 0.0022 | 168.85 |
| 62.000 | 0.003 | 174.298 | 0.0023 | 174.30 |
| 63.000 | 0.003 | 174.298 | 0.0025 | 174.30 |
| 64.000 | 0.004 | 179.745 | 0.0026 | 179.74 |
| 65.000 | 0.004 | 179.745 | 0.0027 | 179.74 |
| 66.000 | 0.004 | 185.192 | 0.0028 | 179.74 |
| 67.000 | 0.004 | 185.192 | 0.0029 | 185.19 |
| 68.000 | 0.004 | 190.638 | 0.0031 | 190.64 |
| 69.000 | 0.004 | 190.638 | 0.0032 | 190.64 |
| 70.000 | 0.004 | 190.638 | 0.0033 | 190.64 |
| 71.000 | 0.004 | 196.085 | 0.0035 | 196.09 |
| 72.000 | 0.004 | 196.085 | 0.0035 | 196.09 |
| 73.000 | 0.004 | 196.085 | 0.0037 | 201.53 |

TABLE 3-continued

Second Calport G Stress v. Deflection Testing

| Time (sec) | Deflection 2 (inches) | Stress 2 (psi) | Deflection 1 (inches) | Stress 1 (psi) |
|---|---|---|---|---|
| 74.000 | 0.004 | 201.532 | 0.0038 | 201.53 |
| 75.000 | 0.004 | 201.532 | 0.0038 | 201.53 |
| 76.000 | 0.004 | 206.979 | 0.0041 | 206.98 |
| 77.000 | 0.004 | 206.979 | 0.0041 | 206.98 |
| 78.000 | 0.005 | 212.426 | 0.0043 | 212.43 |
| 79.000 | 0.005 | 212.426 | 0.0043 | 212.43 |
| 80.000 | 0.005 | 212.426 | 0.0045 | 212.43 |
| 81.000 | 0.005 | 217.872 | 0.0045 | 217.87 |
| 82.000 | 0.005 | 217.872 | 0.0047 | 217.87 |
| 83.000 | 0.005 | 223.319 | 0.0048 | 223.32 |
| 84.000 | 0.005 | 223.319 | 0.0049 | 223.32 |
| 85.000 | 0.005 | 223.319 | 0.0050 | 223.32 |
| 86.000 | 0.005 | 228.766 | 0.0052 | 228.77 |
| 87.000 | 0.005 | 228.766 | 0.0052 | 228.77 |
| 88.000 | 0.005 | 234.213 | 0.0054 | 234.21 |
| 89.000 | 0.005 | 234.213 | 0.0055 | 234.21 |
| 90.000 | 0.006 | 234.213 | 0.0056 | 234.21 |
| 91.000 | 0.006 | 239.660 | 0.0057 | 239.66 |
| 92.000 | 0.006 | 239.660 | 0.0058 | 239.66 |
| 93.000 | 0.006 | 245.106 | 0.0059 | 245.11 |
| 94.000 | 0.006 | 245.106 | 0.0060 | 250.55 |
| 95.000 | 0.006 | 250.553 | 0.0062 | 250.55 |
| 96.000 | 0.006 | 250.553 | 0.0063 | 250.55 |
| 97.000 | 0.006 | 250.553 | 0.0063 | 250.55 |
| 98.000 | 0.006 | 256.000 | 0.0065 | 256.00 |
| 99.000 | 0.006 | 256.000 | 0.0066 | 256.00 |
| 100.000 | 0.006 | 261.447 | 0.0068 | 261.45 |
| 101.000 | 0.006 | 261.447 | 0.0069 | 261.45 |
| 102.000 | 0.007 | 261.447 | 0.0071 | 266.89 |
| 103.000 | 0.007 | 266.894 | 0.0071 | 266.89 |
| 104.000 | 0.007 | 272.340 | 0.0074 | 266.89 |
| 105.000 | 0.007 | 272.340 | 0.0075 | 272.34 |
| 106.000 | 0.007 | 272.340 | 0.0077 | 272.34 |
| 107.000 | 0.007 | 277.787 | 0.0079 | 272.34 |
| 108.000 | 0.007 | 283.234 | 0.0080 | 277.79 |
| 109.000 | 0.007 | 283.234 | 0.0084 | 277.79 |
| 110.000 | 0.007 | 283.234 | 0.0086 | 277.79 |
| 111.000 | 0.007 | 283.234 | 0.0090 | 283.23 |
| 112.000 | 0.008 | 283.234 | 0.0092 | 283.23 |
| 113.000 | 0.008 | 283.234 | 0.0097 | 288.68 |
| 114.000 | 0.008 | 288.681 | 0.0099 | 288.68 |
| 115.000 | 0.008 | 288.681 | 0.0103 | 288.68 |
| 116.000 | 0.008 | 294.128 | 0.0106 | 294.13 |
| 117.000 | 0.008 | 294.128 | 0.0110 | 294.13 |
| 118.000 | 0.008 | 294.128 | 0.0112 | 294.13 |
| 119.000 | 0.008 | 299.574 | 0.0116 | 299.57 |
| 120.000 | 0.009 | 299.574 | 0.0117 | 305.02 |
| 121.000 | 0.009 | 299.574 | 0.0122 | 305.02 |
| 122.000 | 0.009 | 305.021 | 0.0123 | 305.02 |
| 123.000 | 0.009 | 305.021 | 0.0125 | 305.02 |
| 124.000 | 0.009 | 310.468 | 0.0127 | 305.02 |
| 125.000 | 0.009 | 310.468 | 0.0130 | 310.47 |
| 126.000 | 0.010 | 310.468 | 0.0131 | 310.47 |
| 127.000 | 0.010 | 315.915 | 0.0135 | 315.91 |
| 128.000 | 0.010 | 315.915 | 0.0136 | 315.91 |
| 129.000 | 0.010 | 315.915 | 0.0138 | 315.91 |
| 130.000 | 0.010 | 321.362 | 0.0139 | 321.36 |
| 131.000 | 0.011 | 321.362 | 0.0141 | 326.81 |
| 132.000 | 0.011 | 326.809 | 0.0142 | 326.81 |
| 133.000 | 0.011 | 326.809 | 0.0144 | 326.81 |
| 134.000 | 0.011 | 332.255 | 0.0145 | 332.26 |
| 135.000 | 0.011 | 332.255 | 0.0147 | 332.26 |
| 136.000 | 0.012 | 332.255 | 0.0149 | 332.26 |
| 137.000 | 0.012 | 337.702 | 0.0149 | 332.26 |
| 138.000 | 0.012 | 337.702 | 0.0152 | 337.70 |
| 139.000 | 0.012 | 337.702 | 0.0153 | 337.70 |
| 140.000 | 0.012 | 343.149 | 0.0155 | 343.15 |
| 141.000 | 0.012 | 348.596 | 0.0156 | 343.15 |
| 142.000 | 0.013 | 348.596 | 0.0157 | 348.60 |
| 143.000 | 0.013 | 348.596 | 0.0158 | 348.60 |
| 144.000 | 0.013 | 348.596 | 0.0160 | 348.60 |
| 145.000 | 0.013 | 354.043 | 0.0161 | 348.60 |
| 146.000 | 0.013 | 354.043 | 0.0163 | 354.04 |
| 147.000 | 0.013 | 359.489 | 0.0164 | 359.49 |
| 148.000 | 0.013 | 359.489 | 0.0166 | 359.49 |
| 149.000 | 0.014 | 364.936 | 0.0167 | 359.49 |
| 150.000 | 0.014 | 364.936 | 0.0168 | 364.94 |
| 151.000 | 0.014 | 364.936 | 0.0169 | 364.94 |
| 152.000 | 0.014 | 370.383 | 0.0171 | 370.38 |
| 153.000 | 0.014 | 370.383 | 0.0172 | 370.38 |
| 154.000 | 0.014 | 370.383 | 0.0173 | 370.38 |
| 155.000 | 0.014 | 375.830 | 0.0175 | 370.38 |
| 156.000 | 0.014 | 375.830 | 0.0176 | 370.38 |
| 157.000 | 0.015 | 381.277 | 0.0177 | 375.83 |
| 158.000 | 0.015 | 381.277 | 0.0178 | 375.83 |
| 159.000 | 0.015 | 381.277 | 0.0179 | 381.28 |
| 160.000 | 0.015 | 386.723 | 0.0180 | 381.28 |
| 161.000 | 0.015 | 386.723 | 0.0181 | 386.72 |
| 162.000 | 0.015 | 386.723 | 0.0182 | 386.72 |
| 163.000 | 0.015 | 392.170 | 0.0183 | 386.72 |
| 164.000 | 0.015 | 392.170 | 0.0185 | 392.17 |
| 165.000 | 0.015 | 397.617 | 0.0185 | 392.17 |
| 166.000 | 0.016 | 397.617 | 0.0187 | 392.17 |
| 167.000 | 0.016 | 397.617 | 0.0187 | 397.62 |
| 168.000 | 0.016 | 403.064 | | |
| 169.000 | 0.016 | 403.064 | | |
| 170.000 | 0.016 | 403.064 | | |
| 171.000 | 0.016 | 408.511 | | |
| 172.000 | 0.016 | 408.511 | | |
| 173.000 | 0.016 | 408.511 | | |
| 174.000 | 0.016 | 413.957 | | |
| 175.000 | 0.016 | 413.957 | | |
| 176.000 | 0.016 | 413.957 | | |
| 177.000 | 0.017 | 419.404 | | |
| 178.000 | 0.017 | 419.404 | | |
| 179.000 | 0.017 | 419.404 | | |
| 180.000 | 0.017 | 424.851 | | |
| 181.000 | 0.017 | 424.851 | | |
| 182.000 | 0.017 | 430.298 | | |
| 183.000 | 0.017 | 430.298 | | |
| 184.000 | 0.017 | 430.298 | | |
| 185.000 | 0.017 | 435.745 | | |
| 186.000 | 0.017 | 435.745 | | |
| 187.000 | 0.018 | 441.192 | | |
| 188.000 | 0.018 | 441.192 | | |
| 189.000 | 0.018 | 441.192 | | |
| 190.000 | 0.018 | 446.638 | | |
| 191.000 | 0.018 | 446.638 | | |

Figure 17:
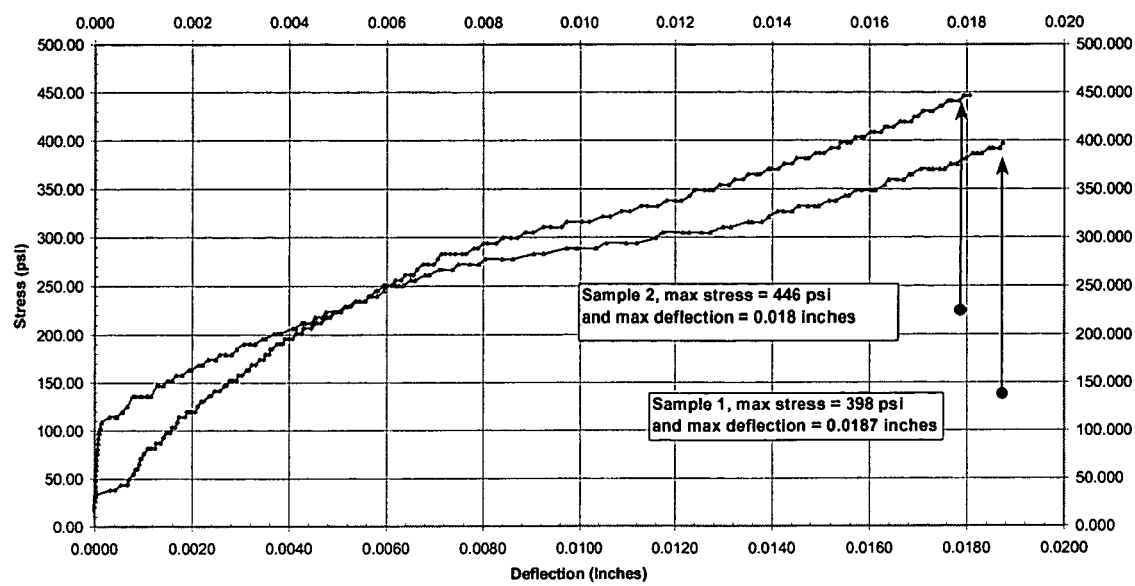
FIG. 17 is a representative graph showing stress versus deflection

As shown in this table, the first specimen bore 397.62 psi and 0.0187 inches deflection while the second specimen boar 446.638 psi 0.018 inches deflection. The data for the first and second specimens have been graphed in FIG. 17. Again, the closeness of this data indicates the consistency of the testing technique. It is envisioned that this consistency will be seen in pressurized experiments.

Those skilled in the art will recognize that the present testing method and apparatus are applicable to any type of cement or cement composition. Examples of suitable hydraulic cement types that may be employed, alone or in mixtures, for wellbore cementing include Portland cements, and more particularly ASTM Type I, II, III, IV and/or V Portland cements, and API Class A, B, C, G and/or H Portland cements, pozzolan cements, Portland cement blends, commercial lightweight cements, slag cements, and microfine cements. Any natural or synthetic material that is substantially elastic, and more particularly that is selected to be substantially elastic under in situ cementing conditions (e.g., downhole well cementing conditions), may be employed. Such materials may be employed in particulate form, and may have individual particles of material may have shapes such as beaded, regular, or irregular shapes, or mixtures thereof. Examples of substantially elastic materials include, but are not limited to, those elastic materials having a Young's modulus of elasticity between about 500 psi and about 2,600,000 psi at anticipated cementing conditions, alternatively between about 500 psi and about 2,000,000 psi at anticipated cementing conditions, alternatively between about 5,000 psi and about 2,000,000 psi at anticipated cementing conditions, alternatively between about 5,000 psi and about 500,000 psi at anticipated cementing conditions, alternatively between about 5,000 psi and 200,000 psi at anticipated cementing conditions, and further alternatively between about 7,000 and 150,000 psi at anticipated cementing conditions. Other examples of substantially elastic materials include, but are not limited to, those elastic materials having a Young's modulus of elasticity between about 500 psi and about 30,000,000 psi at anticipated cementing conditions, alternatively between about 2,000,000 psi and about 30,000,000 psi at anticipated cementing conditions, alternatively between about 2,000,000 psi and about 10,000,000 psi at anticipated cementing conditions, alternatively between about 5,000 psi and about 5,000,000 psi at anticipated cementing conditions, and alternatively between about 7,000 psi and about 1,500,000 psi at anticipated cementing conditions. Yet other examples of substantially elastic materials include, but are not limited to, those elastic materials having a Young's modulus of elasticity between about 500 psi and about 150,000 psi at anticipated cementing conditions. Substantially elastic materials may also have values of Young's modulus of elasticity that are greater than or lesser than those values given in the ranges above.

Having described the invention above, various modifications of the techniques, procedures, material and equipment will be apparent to those in the art. It is intended that all such variations within the scope and spirit of the appended claims be embraced thereby.

What is claimed is:

1. A tester capable of determining Young's modulus for a cement specimen comprising:
    a pressure chamber;
    at least one mold body disposed in the pressure chamber, wherein the mold comprises:
        a stationary portion of the mold body;
        a pulled portion of the mold body;
    a follower attached to the pulled portion of the mold body capable of imparting axial stress and axial strain on the specimen;
    a ram capable of producing a load at a predetermined rate that is transferred to the follower;
    a load cell capable of measuring axial stress on the specimen;
    a linear displacement transducer capable of measuring axial strain on the specimen;
    a least one data acquisition unit capable of recording the axial stress and axial strain on the specimen.

2. The tester of claim 1 wherein the mold body further comprises a floating section.

3. The tester of claim 1 further comprising a cam and a piston, wherein the piston extends into the pressure chamber.

4. The tester of claim 1 further comprising at least one linear transducer.

5. The tester of claim 1 further comprising at least one thermocouple.

6. The tester of claim 1 further comprising at least one pressure transducer.

7. A processor capable of calculating Young's moduluses for a corresponding plurality of cement specimens using the tester of claim 1 the tester comprising:
    a plurality of mold bodies equal to the number of specimens disposed in the at least one pressure chamber; and
    a follower attached to each pulled portion of each mold body capable of imparting axial stress and strain on the specimen.

8. The multitester of claim 7 wherein the load cell imparts a load on each follower in a sequential order.

* * * * *